United States Patent
Nomura et al.

(10) Patent No.: US 6,780,431 B1
(45) Date of Patent: Aug. 24, 2004

(54) SUBSTITUTED BENZYLTHIAZOLIDINE-2,4-DIONE DERIVATIVES

(75) Inventors: Mashiro Nomura, Nogi-machi (JP); Koji Murakami, Oyama (JP); Masaki Tsunoda, Kasukabe (JP); Yukie Takahashi, Nogi-machi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 88 days.

(21) Appl. No.: 10/049,937
(22) PCT Filed: Aug. 18, 2000
(86) PCT No.: PCT/JP00/05522
§ 371 (c)(1), (2), (4) Date: Feb. 20, 2002
(87) PCT Pub. No.: WO01/14352
PCT Pub. Date: Mar. 1, 2001

(30) Foreign Application Priority Data

Aug. 23, 1999 (JP) ............................. 11-235530

(51) Int. Cl.[7] .................. A61K 31/426; A61K 9/20; A61P 3/06; C07D 277/30
(52) U.S. Cl. .................. 424/464; 514/369; 548/183
(58) Field of Search .................. 514/368; 548/183

(56) References Cited

FOREIGN PATENT DOCUMENTS

| EP | 0 332 331 | 9/1989 |
|---|---|---|
| EP | 881219 | 12/1998 |
| JP | 8-333355 | 12/1996 |
| JP | 9-48771 | 2/1997 |
| JP | 0 846 693 | * 6/1998 |
| WO | 97/32863 | 9/1997 |

OTHER PUBLICATIONS

K. Murakami et al.: "A Novel Insulin Sensitizer Acts as a Coligand for Peroxisome Proliferator–Activated Receptor–a (PPAR–a) and PPAR–y" DIABETES, 47, pp. 1841–1847, 1998.

Ide Tomohiro et al.: "Zuker fatty Rat ni okeru Kanshishitsu Taisha taisuru PPAR a Kasseika no Eikyou" Diabetes Frontier, 9(3), pp. 345–346, 1998.

Momura et al., "(3–Substituted benzyl)thiazolidine–2,4–diones as structurally new antihyperglycemic agents" Bioorganic & Medicinal Chemistry Letters, vol. 9, No. 4., 22 Feb. 22, 1999, pp 533–538.

* cited by examiner

Primary Examiner—Joseph K. McKane
Assistant Examiner—Sonya Wright
(74) Attorney, Agent, or Firm—Oblon, Spivak, McClelland, Maier & Neustadt, P.C.

(57) ABSTRACT

The invention relates to substituted benzylthiazolidine-2,4-dione derivatives represented by a general formula (1)

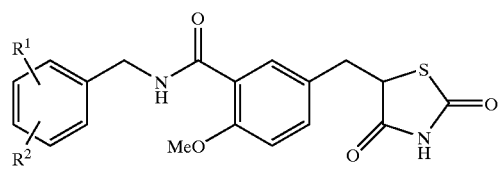

wherein $R^1$ denotes a chlorine atom, bromine atom, nitro group, trifluoromethoxy group, ethoxy group, propoxy group or isopropoxy group, and $R^2$ denotes a hydrogen atom or chlorine atom, their medicinally acceptable salts, their hydrates and a process for preparing them.

27 Claims, No Drawings

SUBSTITUTED BENZYLTHIAZOLIDINE-2,4-DIONE DERIVATIVES

This application is a 371 of PCT/JP00/05522 filed Aug. 18, 2000.

TECHNICAL FIELD

The present invention relates to substituted benzylthiazolidine-2,4-dione derivatives effective for the prevention and/or therapy of metabolic diseases such as diabetes and hyperlipidemia as agonists of peroxisome proliferator-activated receptor (abbreviated as PPAR) being nuclear receptor, in particular, as agonists of human PPAR, their addition salts, process for preparing them, and medicinal compositions containing these compounds.

BACKGROUND TECHNOLOGIES

The peroxisome proliferator-activated receptor(PPAR) is a ligand-dependent transcription factor that belongs to nuclear receptor superfamily similarly to steroid receptor, retinoid receptor, thyroid receptor, etc., and three isoforms (α type, β (or δ) type and γ type) with different histological distribution have been identified hitherto in human and various animal species (Proc. Natl. Acad. Sci., 1992, 89, 4653). Thereamong, the PPARα is distributed in the liver, kidney, etc. with high catabolic capacity for fatty acids and, particularly high expression is recognized in the liver, (Endo-crinology, 1995, 137, 354), positively or negatively controlling the expressions of genes related to the metabolism and the intracellular transport of fatty acids (e.g. acyl CoA synthetic enzyme, fatty acid-binding protein and lipoprotein lipase) and apolipoprotein (AI, AII, CIII) genes related to the metabolisms of cholesterol and neutral lipid. The PPARβ is expressed ubiquitously in the tissues or organisms centering around nerve cells. At present, the physiological significance of PPARβ is unclear. The PPARγ is highly expressed in the adipocytes and contributed to the differentiation of adipocytes (J. Lipid Res., 1996, 37, 907). In this way, each isoform of PPAR play specific functions in the particular organs and tissues.

Moreover, it is reported that a knock-out mouse of PPARα exhibits hypertriglyceridemia with ageing and becomes obesity mainly by increasing the white adipocytes (J. Biol. Chem., 1998, 273, 29577), hence the relevance between activation of PPARα and decreasing action of lipids (cholesterol and triglyceride) in blood is suggested strongly.

On the other hand, fibrates and statins are widely used so far as the therapeutic drugs for hyperlipidemia. However, the fibrates have only weak decreasing action of cholesterol, while the statins have weak decreasing action of free fatty acids and triglycerides. Moreover, with respect to the fibrates, various adverse effects such as gastrointestinal injury, anthema, headache, hepatic disorder, renal disorder and biliary calculus are reported. The reason is considered to be due to that the fibrates exhibit extensive pharmacological function.

On the other hand, it is ascertained that the major intracellular target protein of Troglitazone, Pioglitazone and Rosiglitazone being a series of thiazolidine-2,4-dione derivatives that are therapeutic drugs for type II diabetes (noninsulin-dependent diabetes) and exhibit blood glucose-decreasing action, improving action on hyperinsulinemia, etc. is PPARγ, and these drugs increase the transactivation of PPARγ (Endocrinology, 1996, 137, 4189, Cell., 1995, 83, 803, Cell., 1995, 83, 813). Hence, PPARγ-activator (agonist) that can augment the transactivation of PPARγ is important as antidiabetic drug.

As described, when considering the roles of transcription factor called PPAR on the function on adipocytes and the controlling mechanisms of glucose metabolism and lipid metabolism, if a compound that binds directly to as a ligand of PPAR, in particular, human PPAR and can activate human PPAR could be created, it would be reasonable to expect the medicinal use as a compound that exhibits blood glucose-decreasing action and/or decreasing action of lipids (both of cholesterol and triglyceride) in blood due to very specific mechanism.

For compounds having an affinity to PPARα as ligands of PPARα, HEPE (hydroxyeicosapentaenoic acid) produced via oxidation with cytochrome P-450 and eicosanoides in HETE (hydroxyeicosatetraenoic acid) groups, in particular, 8-HETE, 8-HEPE, etc. are reported in addition to LTB., being a metabolite of arachidonic acid (Proc. Natl. Acad. Sci., 1997, 94, 312). However, these endogenous unsaturated fatty acid derivatives are unstable metabolically and chemically and cannot be offered as medicinal drugs.

Moreover, with Troglitazone, the occurrence of serious adverse effect on liver is reported rarely, hence the development of a therapeutic drug for type II diabetes with effectiveness and high safety is being sought.

Now, as compounds with similar structure to the inventive substituted benzylthiazolidine-2,4-dione derivatives, thiazolidine-2,4-dione derivatives in Japanese Unexamined Patent Publication Nos. Sho 55-22636, Sho 60-51189, Sho 61-85372, Sho 61-286376, Hei 1-131169, Hei 2-83384, Hei 5-213913, Hei 8-333355, Hei 9-48771 and Hei 9-169746, European Patent Open No. 0441605, WO-92/07839, etc. are known. However, all of these compounds are thiazolidine-2,4-dione derivatives with different structure from the inventive compounds.

With regard to patents etc. reporting the agonistic effect on PPAR α, WO-97/25042, WO-97/36579, etc. are reported, but all of these have different structure from the inventive compounds and the transactivation function of PPARα is also never satisfied in strength.

Both the hyperlipidemia and the diabetes are risk factors of arterosclerosis and, from a viewpoint of the prevention of arterosclerosis, in particular, coronary arterosclerosis, the development of a therapeutic drug for metabolic diseases with effectiveness and high safety is desired clinically.

DISCLOSURE OF THE INVENTION

As a result of diligent studies paying an attention to such specific roles on the lipid metabolism of human PPAR, differentiation of adipocytes, etc. aiming at the creation of structurally novel drug with effectiveness and high safety as a therapeutic drug for metabolic diseases, the inventors have found that novel substituted benzylthiazolidine-2,4-dione derivatives represented by the following general formula (1) have excellent transactivation function of human PPAR, and exhibit the blood glucose-decreasing action and the lipid-decreasing action, leading to the completion of the invention.

Namely, the invention relates to the substituted benzylthiazolidine-2,4-dione derivatives represented by the general formula (1)

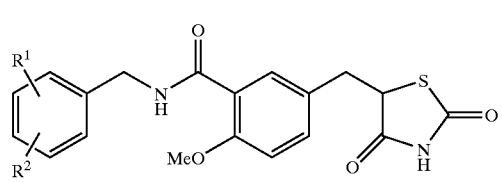

(1)

[wherein R¹ denotes a chlorine atom, bromine atom, nitro group, trifluoromethoxy group, ethoxy group, propoxy group or isopropoxy group, and R² denotes a hydrogen atom or chlorine atom], their medicinally acceptable salts and their hydrates.

The salts of the compounds represented by the general formula (1) in the invention are of common use and metal salts, for example, alkali metal salts (e.g. sodium salt, potassium salt, etc.), alkaline earth metal salts (e.g. calcium salt, magnesium salt, etc.), aluminum salt, and other pharmacologically acceptable salts are mentioned.

Furthermore, for the compounds represented by the general formula (1), the existence of various tautomers is considered. These are, for example, as shown in the following formulae.

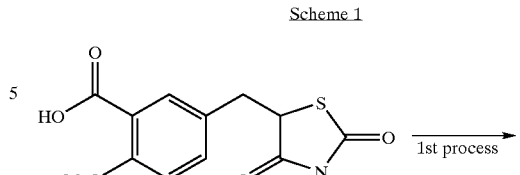

Scheme 1

(2)

(1)

Namely, the compounds represented by the general formula (1) can be prepared by reacting (first process) publicly known (Japanese Unexamined Patent Publication No. Hei 8-333355) compound (2) and the compounds represented by the general formula (3)

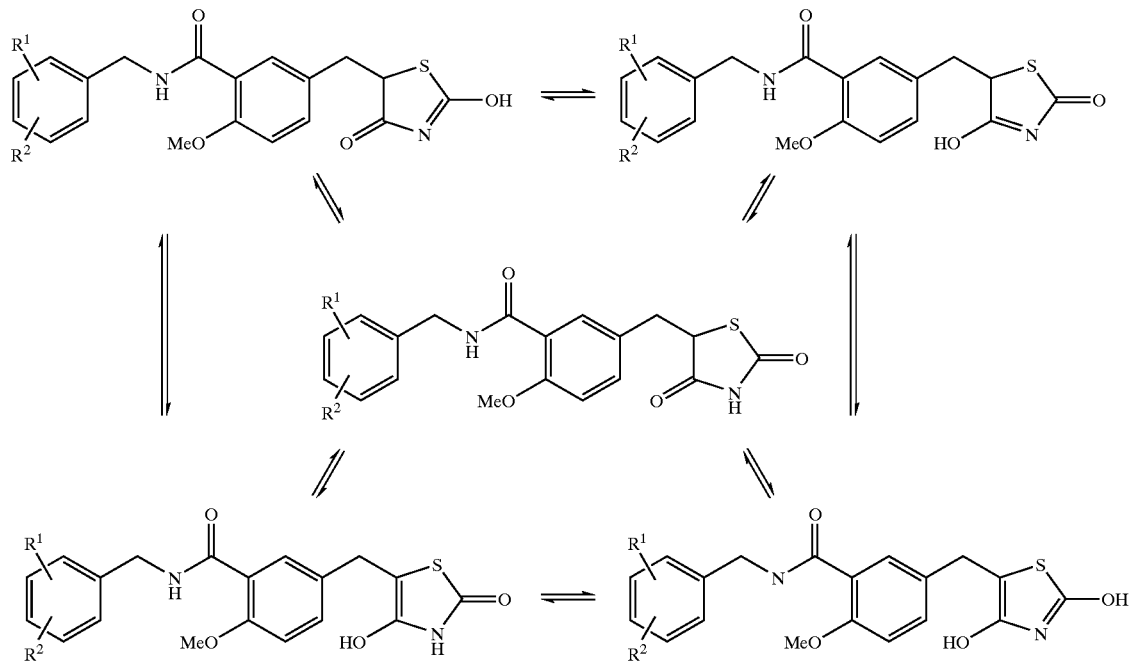

[wherein R¹ denotes a chlorine atom, bromine atom, nitro group, trifluoromethoxy group, ethoxy group, propoxy group or isopropoxy group, and R² denotes a hydrogen atom or chlorine atom]. In the general formula (1) aforementioned, all of these isomers and their mixtures are to be included in the scope of this invention.

According to the invention, the compounds being said the general formula (1) can be prepared, for example, through the following process (Scheme 1).

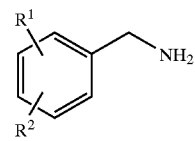

(3)

[wherein R¹ denotes a chlorine atom, bromine atom, nitro group, trifluoromethoxy group, ethoxy group, propoxy group or isopropoxy group, and R² denotes a hydrogen atom or chlorine atom].

The first process can be performed by the leaving carboxyl group as it is, or converting it to the reactive derivative.

As the "reactive derivative group of the carboxyl group", acid chloride, acid bromide, acid anhydride, carbonylimidazole or the like can be mentioned. In the case of the reaction using the reactive derivative, the reaction can be performed in a solvent such as methylene chloride, chloroform, dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving the carboxylic acid as it is, the reaction can be performed in a solvent such as methylene chloride, chloroform, dioxane or N,N-dimethylformamide in the presence of condensing agent in the presence or absence of base, in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate; or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of −20° C. to 100° C., preferably at 0° C. to 50° C.

As the administering form of the novel compounds of the invention, for example, oral administration with tablet, capsule, granule, powder, inhalant, syrup or the like, or parenteral administration with injection, suppository or the like can be mentioned.

BEST EMBODIMENT TO PUT THE INVENTION INTO PRACTICE

In following, the invention will be illustrated based on concrete examples, but the invention is not confined to these examples.

EXAMPLE 1

N-[(4-Nitrophenyl)methyl]-5-[(2,4-dioxothiazolidin-5-yl)methyl]-2-methoxybenzamide 5-[(2,4-Dioxothiazolidin-5-yl)methyl]-2-methoxybenzoic acid (422 mg, 1.50 mmol), triethylamine (0.732 mL, 5.25 mmol) and methylene chloride (7 mL) were mixed and ethyl chlorocarbonate (0.158 mL, 1.50 mmol) was added under cooling with ice and stirring. After stirring for 10 minutes under cooling with ice, 4-nitrobenzylamine (283 mg, 1.50 mmol) was added. The mixture was stirred for 2 hours at room temperature, and then allowed to stand overnight. After washed with water, the reaction mixture was dried over anhydrous sodium sulfate and concentrated. The residue was dissolved into water (20 mL), which was made acidic with 10% hydrochloric acid and stirred for 2 hours. The precipitated crystals were collected by filtration, washed with water and dried, then they were recrystallized from ethanol to obtain 472 mg (75%) of the title compound as pale yellow prisms.

Melting point 236.5–238.5° C.;

Mass analysis m/z 415(M$^+$);

Elemental analysis(%) $C_{19}H_{17}N_3O_6S$: Calcd.(%) C, 54.93; H, 4.12; N, 10.12. Found (%) C, 54.84; H, 4.14; N, 9.98.

EXAMPLES 2 THROUGH 9

Similarly to Example 1, the compounds shown in Table 1 were obtained.

TABLE 1

| Example | R$^1$ | R$^2$ | Melting point (° C.) | Charac. formula | Elemental analysis (%) | | |
|---|---|---|---|---|---|---|---|
| 2 | 4-Br | H | 198.0–200.0 | $C_{19}H_{17}BrN_2O_4S$ | Cald.; C 50.79, | H 3.81, | N 6.23 |
|   |      |   |             |                         | Found; C 50.75, | H 3.75, | N 6.16 |
| 3 | 4-Cl | H | 199.0–201.0 | $C_{19}H_{17}ClN_2O_4S$ | Cald.; C 56.36, | H 4.23, | N 6.92 |
|   |      |   |             |                         | Found; C 56.27, | H 4.24, | N 6.82 |
| 4 | 3-CF$_3$O | H | Amorphous | $C_{20}H_{17}F_3N_2O_5S$ | Cald.; C 52.86, | H 3.77, | N 6.16 |
|   |      |   |             |                         | Found; C 52.82, | H 3.75, | N 6.08 |
| 5 | 4-EtO | H | 130.0–132.0 | $C_{21}H_{22}N_2O_5S$ | Cald.; C 60.85, | H 5.35, | N 6.76 |
|   |      |   |             |                         | Found; C 60.87, | H 5.30, | N 6.73 |
| 6 | 4-iPrO | H | 79.0–81.5 | $C_{22}H_{24}N_2O_5S \cdot H_2O$ | Cald.; C 59.18, | H 5.87, | N 6.27 |
|   |      |   |             |                         | Found; C 59.27, | H 5.74, | N 6.28 |
| 7 | 4-nPrO | H | 132.0–133.0 | $C_{22}H_{24}N_2O_5S \cdot 1/5H_2O$ | Cald.; C 61.15, | H 5.69, | N 6.48 |
|   |      |   |             |                         | Found; C 61.03, | H 5.51, | N 6.37 |
| 8 | 4-Cl | 2-Cl | 188.0–189.0 | $C_{19}H_{16}Cl_2N_2O_4S \cdot 1/5H_2O$ | Cald.; C 51.52, | H 3.73, | N 6.32 |
|   |      |   |             |                         | Found; C 51.63, | H 3.60, | N 6.29 |
| 9 | 4-Cl | 3-Cl | 181.0–182.0 | $C_{19}H_{16}Cl2N_2O_4S \cdot 1/5H_2O$ | Cald.; C 51.52, | H 3.73, | N 6.32 |
|   |      |   |             |                         | Found; C 51.45, | H 3.55, | N 6.30 |

<Biological activity>

TEST EXAMPLE 1

Test of Transactivation on Peroxisome Proliferator-activated Receptors α and β

To CHO cells cultured in a Ham's F-12 medium containing fatty acid free 10% fetal calf serum, receptor plasmid and its reporter plasmid (STRATAGENE Corp.) that express fused protein of DNA-binding domain being transcription factor of yeast with ligand-binding domain of human type PPARs α and β (Biochemistry, 1993, 32, 5598), and β-galactosidase plasmid (Promega Corp.) for internal standard were cotransfected with lipofectamine in the serum-free state. Thereafter, testing compound and control compound (Troglitazone or Pioglitazone for control drug of PPARγ, and (8S)-HETE for control drug of PPARα) were dissolved into DMSO and adjusted with Ham's F-12 medium containing fatty acid free 10% fetal calf serum, so that the final concentration of DMSO became 0.01% to culture. After 24 hours, CAT activity and β-galactosidase activity were measured.

Results are shown in Table 2. From these results, it was shown that the inventive compounds had potent transactivation action on human peroxisome proliferator-activated receptors α and γ.

TABLE 2

| | Transactivation | |
|---|---|---|
| Example | PPARα $EC_{50}$ (μmol/L) | PPARγ $EC_{50}$ (μmol/L) |
| 1 | 0.53 | 1.6 |
| 2 | 0.49 | 0.29 |
| 3 | 0.26 | 0.40 |
| 4 | 0.18 | 0.36 |
| 5 | 0.43 | 0.30 |
| 6 | 0.76 | 0.11 |
| 7 | 0.11 | 1.8 |
| 8 | 0.22 | 0.28 |
| 9 | 0.70 | 1.1 |
| Troglitazone | — | 1.15 |
| Pioglitazone | — | 0.72 |
| (8S)-HETE | 1.30 | — |

UTILIZABILITY IN THE INDUSTRY

From the results as descried above, the inventive substituted benzylthiazolidine-2,4-dione derivatives are novel compounds with excellent human PPAR transactivation.

From the fact that these inventive compounds have agonistic activity on human PPAR, it can be said that they are effective compounds as blood glucose-decreasing drugs and therapeutic drugs for hyperlipidemia aforementioned.

What is claimed is:

1. N-[(4-ethoxyphenyl)methyl]-5-[(2,4-dioxothiazolidin-5-yl)methyl]-2-methoxybenzamide, or a medicinally acceptable salt or hydrate thereof.

2. N-[(4-chlorophenyl)methyl]-5-[(2,4-dioxothiazolidin-5-yl)methyl]-2-methoxybenzamide, or a medicinally acceptable salt or hydrate thereof.

3. N-[(2,4-dichlorophenyl)-methyl]-5-[(2,4-dioxothiazolidin-5-yl)methyl]-2-methoxybenzamide, or a medicinally acceptable salt or hydrate thereof.

4. A tablet, capsule, granule, powder, inhalant, syrup, injectable composition, or suppository, comprising a substituted benzylthiazolidine-2,4-dione derivative represented by the formula (1):

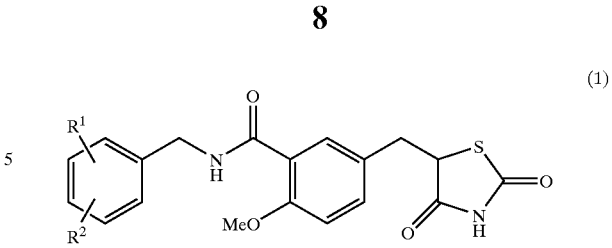

(1)

wherein
either
R$^1$ denotes a 4-chloro, 3-trifluromethyl, or 4-ethoxy substituent, and
R$^2$ denotes a hydrogen atom,
or
R$^1$ denotes a 4-chloro substituent, and
R$^2$ denotes a 2-chloro substituent,
or a medicinally acceptable salt or hydrate thereof.

5. The tablet, capsule, granule, powder, inhalant, syrup, injectable composition, or suppository of claim 4, wherein R$^1$ denotes a 4-chloro, 3-trifluromethyl, or 4-ethoxy substituent, and R$^2$ denotes a hydrogen atom, or a medicinally acceptable salt or hydrate thereof.

6. The tablet, capsule, granule, powder, inhalant, syrup, injectable composition, or suppository of claim 4, wherein the substituted benzylthiazolidine-2,4-dione derivative is N-[(3-trifluoromethoxyphenyl)methyl]-5-[(2,4-dioxothiazolidin-5-yl)methyl]-2-methoxybenzamide or a medicinally acceptable salt or hydrate thereof.

7. The tablet, capsule, granule, powder, inhalant, syrup, injectable composition, or suppository of claim 4, wherein the substituted benzylthiazolidine-2,4-dione derivative is N-[(4-ethoxyphenyl)methyl]-5-[(2,4-dioxothiazolidin-5-yl)methyl]-2-methoxybenzamide or a medicinally acceptable salt or hydrate thereof.

8. The tablet, capsule, granule, powder, inhalant, syrup, injectable composition, or suppository, wherein the substituted benzylthiazolidine-2,4-dione derivative is N-[(4-chlorophenyl)methyl]-5-[(2,4-dioxothiazolidin-5-yl)methyl]-2-methoxybenzamide or a medicinally acceptable salt or hydrate thereof.

9. A tablet, capsule, granule, powder, inhalant, syrup, injectable composition, or suppository, wherein the substituted benzylthiazolidine-2,4-dione derivative is N-[(2,4-dichlorophenyl)-methyl]-5-[(2,4dioxothiazolidin-5-yl)methyl]-2-methoxybenzamide or a medicinally acceptable salt or hydrate thereof.

10. A method of reducing blood glucose, comprising administering an effective amount of N-[(4-ethoxyphenyl)methyl]-5-[(2,4-dioxothiazolidin-5-yl)methyl]-2-methoxybenzamide or a medicinally acceptable salt or hydrate thereof to a subject in need thereof.

11. A method of treating hyperlipidemia, comprising administering an effective amount of N-[(4-ethoxyphenyl)methyl]-5-[(2,4-dioxothiazolidin-5-yl)methyl]-2-methoxybenzamide, or a medicinally acceptable salt or hydrate thereof to a subject in need thereof.

12. A method of reducing blood glucose, comprising administering an effective amount of N-[(4-chlorophenyl)methyl]-5-[(2,4-dioxothiazolidin-5-yl)methyl]-2-methoxybenzamide or a medicinally acceptable salt or hydrate thereof to a subject in need thereof.

13. A method of treating hyperlipidemia, comprising administering an effective amount of N-[(4-chlorophenyl)methyl]-5-[(2,4-dioxothiazolidin-5-yl)methyl]-2-methoxybenzamide or a medicinally acceptable salt or hydrate thereof to a subject in need thereof.

14. A method of reducing blood glucose, comprising administering an effective amount of N-[(2,4-dichlorophenyl)-methyl]-5-[(2,4-dioxothiazolidin-5-yl)methyl]-2-methoxybenzamide or a medicinally acceptable salt or hydrate thereof to a subject in need thereof.

15. A method of treating hyperlipidemia, comprising administering an effective amount of N-[(2,4-dichlorophenyl)-methyl]-5-[(2,4-dioxothiazolidin-5-yl)methyl]-2-methoxybenzamide or a medicinally acceptable salt or hydrate thereof to a subject in need thereof.

16. A method of reducing blood glucose, comprising administering an effective amount of the tablet, capsule, granule, powder, inhalant, syrup, injectable composition, or suppository of claim 4 to a subject in need thereof.

17. A method of reducing blood glucose, comprising administering an effective amount of the tablet, capsule, granule, powder, inhalant, syrup, injectable composition, or suppository of claim 5 to a subject in need thereof.

18. A method of reducing blood glucose, comprising administering an effective amount of the tablet, capsule, granule, powder, inhalant, syrup, injectable composition, or suppository of claim 6 to a subject in need thereof.

19. A method of reducing blood glucose, comprising administering an effective amount of the tablet, capsule, granule, powder, inhalant, syrup, injectable composition, or suppository of claim 7 to a subject in need thereof.

20. A method of reducing blood glucose, comprising administering an effective amount of the tablet, capsule, granule, powder, inhalant, syrup, injectable composition, or suppository of claim 8 to a subject in need thereof.

21. A method of reducing blood glucose, comprising administering an effective amount of the tablet, capsule, granule, powder, inhalant, syrup, injectable composition, or suppository of claim 9 to a subject in need thereof.

22. A method of treating hyperlipidemia, comprising administering an effective amount of the tablet, capsule, granule, powder, inhalant, syrup, injectable composition, or suppository of claim 4 to a subject in need thereof.

23. A method of treating hyperlipidemia, comprising administering an effective amount of the tablet, capsule, granule, powder, inhalant, syrup, injectable composition, or suppository of claim 5 to a subject in need thereof.

24. A method of treating hyperlipidemia, comprising administering an effective amount of the tablet, capsule, granule, powder, inhalant, syrup, injectable composition, or suppository of claim 6 to a subject in need thereof.

25. A method of treating hyperlipidemia, comprising administering an effective amount of the tablet, capsule, granule, powder, inhalant, syrup, injectable composition, or suppository of claim 7 to a subject in need thereof.

26. A method of treating hyperlipidemia, comprising administering an effective amount of the tablet, capsule, granule, powder, inhalant, syrup, injectable composition, or suppository of claim 8 to a subject in need thereof.

27. A method of treating hyperlipidemia, comprising administering an effective amount of the tablet, capsule, granule, powder, inhalant, syrup, injectable composition, or suppository of claim 9 to a subject in need thereof.

\* \* \* \* \*